United States Patent [19]

Tsuji

[11] Patent Number: 4,582,686
[45] Date of Patent: Apr. 15, 1986

[54] APPARATUS FOR ANALYZING ELEMENTS CONTAINED IN METAL COMPOSITIONS

[75] Inventor: Katsuya Tsuji, Kyoto, Japan

[73] Assignee: Horiba, Ltd., Kyoto, Japan

[21] Appl. No.: 544,408

[22] Filed: Oct. 20, 1983

[30] Foreign Application Priority Data

Nov. 4, 1982 [JP]  Japan ............................... 57-194217
Nov. 27, 1982 [JP] Japan ............................... 57-210438

[51] Int. Cl.[4] .......................................... G01N 31/12
[52] U.S. Cl. ...................................... 422/80; 436/160
[58] Field of Search .......................... 422/78, 80, 157; 436/160, 155; 431/189, 186

[56] References Cited

U.S. PATENT DOCUMENTS 3,497,322  2/1970  Boys ....................................... 422/80
3,681,031  8/1972  Johnson ............................... 422/157
3,847,554  11/1974 Su .......................................... 422/80
3,985,505  10/1976 Bredeweg ........................... 436/155
4,234,315  11/1980 Scott .................................. 422/78 X
4,493,271  1/1985  Ohayon et al. ................. 431/186 X
4,498,861  2/1985  Suzuki et al. .................... 431/189 X Primary Examiner—Kenneth M. Schor
Attorney, Agent, or Firm—Wenderoth, Lind & Ponack

[57] ABSTRACT

An apparatus for analyzing elements in metal containing compositions which includes a combustion furnace for combusting a metal composition to be analyzed, a combustion gas feed pipe for feeding combustion gas into the furnace toward the metal composition for promoting combustion thereof, a gas analyzer for analyzing the combusted gas obtained by the combustion of the metal composition in the furnace, a combusted gas conduit between the furnace and the gas analyzer, a carrier gas feed conduit for directing a carrier gas into the furnace so as to carry the combusted gas from the furnace to the gas analyzer through the combusted gas conduit, and structure for changing the rate at which the combustion gas is fed to the metal composition.

8 Claims, 2 Drawing Figures

APPARATUS FOR ANALYZING ELEMENTS CONTAINED IN METAL COMPOSITIONS

BACKGROUND OF THE INVENTION

1. Field of the Invention

The present invention relates to an apparatus for analyzing elements contained in metal compositions such alloys, and more particularly to such an apparatus in which the metal composition is combusted in a furnace and the combusted gas is extracted from the furnace and introduced into a gas analyzer.

2. Description of the Prior Art

Apparatuses of the above described type for analyzing the carbon, sulfur or like contents of metal containing compositions are known. In such known apparatuses, oxygen is directed into the combustion furnace at a fixed rate toward the composition to be analyzed, in order to support combustion of the composition. However, depending on the particular composition being analyzed, which composition is typically held in a crucible or on a platform, and the particular stage of combustion thereof, the amount of oxygen gas directed thereto may cause the composition to splash out of the crucible or be bumped off of the platform, resulting in unreliable analytical results from the analysis. Further, during the combustion process, again depending on the particular composition being analyzed and the stage of combustion, large amounts of dust can be created during the combustion process. This can occur because, for the particular composition being analyzed and the particular stage of the combustion process, the oxygen flow directed toward the composition may be excessive in overall flow rate or speed. Such dust can absorb some of the combusted gas, whereby the accuracy of the analysis is reduced.

OBJECTS AND SUMMARY OF THE INVENTION

It is therefore an object of the present invention to provide an apparatus for analyzing elements in a metal containing composition in which the above-described defects of conventional apparatuses are overcome by controlling the flow rate and/or speed of the oxygen directed toward the composition for purposes of combustion, depending on the particular type of composition to be analyzed and the stage of the combustion process.

In accordance with one embodiment of the invention, an oxygen supply conduit having branches respectively opening into the furnace for concurrently directing oxygen gas to the metal composition for promoting combustion and directing oxygen gas into the furnace so as to carry the combusted gas from the furnace to the gas analyzer. In this preferred embodiment, the rate at which oxygen gas is directed to the metal composition for combustion purposes is controlled with (1) a flow controller disposed in one of the branches for controlling the rate of oxygen flow therethrough and therefore the relative flow rate in one branch relative to the other, (2) a plurality of feed pipes of different calibers which can be selected for directing the oxygen gas into the furnace for combustion purposes by a passage changeover mechanism, so as to control the speed and flow rate of the oxygen gas through said one feed pipe, and (3) drive means for alternatively moving the feed pipes toward or away from the metal composition.

In accordance with another aspect of the invention a controlling mechanism is coupled to the change-over mechanism, the drive means and the flow controller for automatically controlling the ratio of oxygen gas flow in the branch which provides combustion oxygen to the composition, the rate at which the oxygen gas is fed to the metal composition through one of the feed pipes, and the speed of oxygen flow toward the metal composition during and after passing through the one of the feed pipes.

BRIEF DESCRIPTION OF THE DRAWINGS

These and other aspects of the invention will be better understood from the following detailed description of the preferred embodiment when taken with the accompanying drawings, in which.

DETAILED DESCRIPTION OF THE PREFERRED EMBODIMENT

Figure 1:
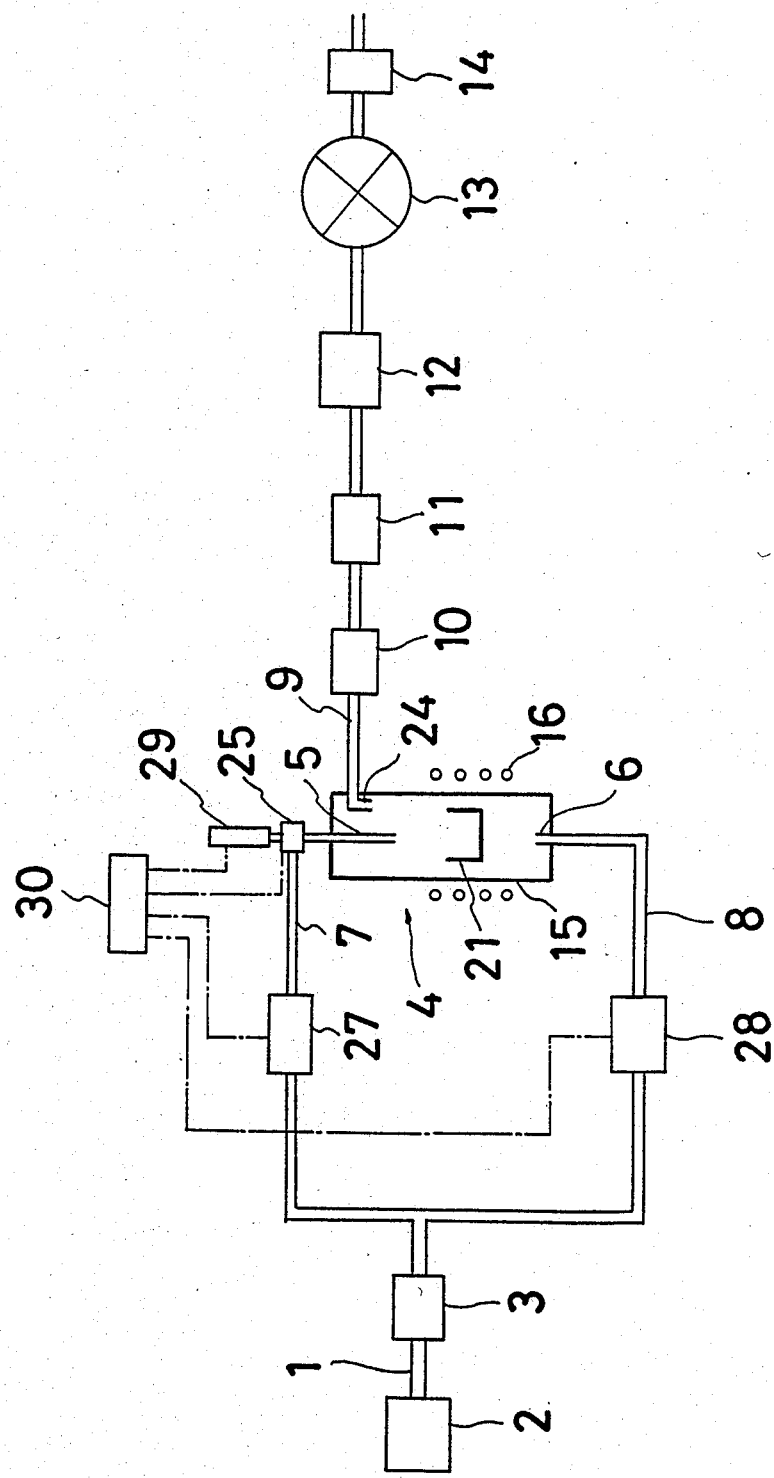
FIG. 1 is a schematic drawing of an apparatus for analyzing elements in a metal containing composition in accordance with the invention.

Referring to FIG. 1 which is a schematic illustration of an apparatus for analyzing elements contained in a metal containing composition in accordance with the present invention, a feed passage 1 is connected at one end to a source 2 of oxygen gas and at its opposite end branches into a combustion gas branch 7 and a carrier gas branch 8. A refiner 3 is provided in feed passage 1.

A number of feed pipes 5 are provided at the end of combustion gas branch 7 for providing combustion gas downwardly through the top of a furnace 4 for supporting combustion of a composition to be analyzed held in a crucible 21 within the furnace. A carrier gas feed pipe 6 is provided at the end of carrier gas branch 8 so as to direct carrier gas (a portion of the oxygen flowing in feed passage 1 from oxygen source 2) through the bottom of furnace 4.

An exhaust pipe or passage 24 is provided at the top end of furnace 4 for carrying away the combusted gas resulting from combustion of the composition in crucible 21 with the carrier gas which flows upwards through the furnace from carrier gas feed pipe 6. A combusted gas feed tube 9 connected to the exhaust pipe 24 carries the exhausted combusted gas and carrier gas successively through a dust filter 10, dewatering portion 11, flow controller 12, gas analyzer 13 and flow meter 14 before venting the gasses from the apparatus. The gas analyzer 13 typically includes an infrared X-ray detector for detecting carbon dioxide and sulfur dioxide which would be in the combusted gas where carbon and sulfur are contained in the composition being analyzed.

Figure 2:
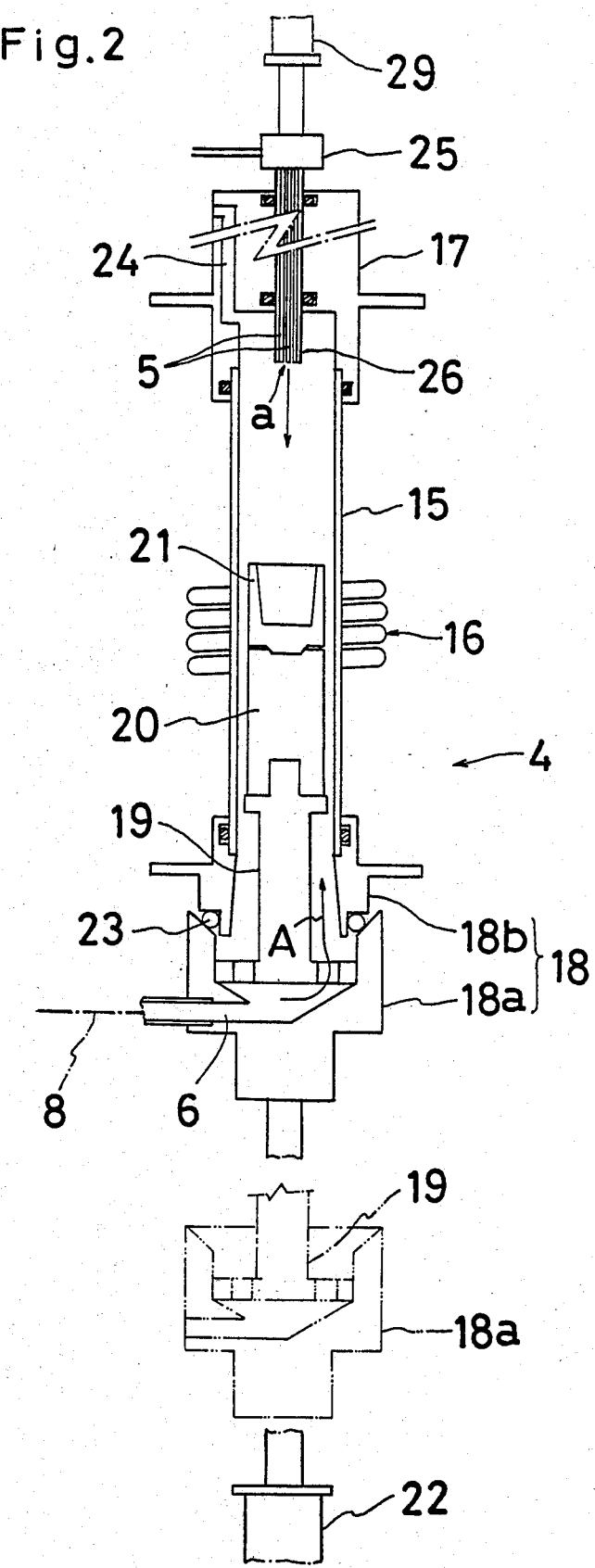
FIG. 2 is a sectional view showing the combustion furnace in accordance with the present invention.

The construction of the combustion furnace 4, which is best illustrated in FIG. 2, includes a cylindrical combustion tube 15 such as a quartz tube surrounded by an induction coil 16 at the middle portion thereof. Cover members 17 and 18 are respectively mounted through O-rings at the upper and lower ends of the combustion tube 15 in order to respectively close the upper and lower ends of the combustion tube 15.

Lower cover member 18 includes a centrally open upper portion 18b sealingly mounted to the bottom end of combustion tube 15 with an O-ring. A cover member lower portion 18a is sealingly held against the bottom of upper portion 18b through O-ring 23 by a drive cylinder 22, so as to removably close the bottom end of combustion tube 15. Carrier gas feed pipe 6 is mounted in a horizontal opening in lower cover member lower portion 18a which communicates with a turned-up gas passage A and combustion tube 15, whereby the carrier gas is directed upward through the combustion tube 15. Mounted centrally on lower cover member lower portion 18a so as to extend through the central opening in upper portion 18b into the combustion tube 15 is a metallic stand 19. A ceramic stand 20 is mounted on the metallic stand 19 and a crucible 21 formed of porcelain is provided on the ceramic stand 20 for supporting the metal containing composition to be analyzed substantially in the center of the induction coil 16. Excitation of induction coil 16 directs radiant heat to the composition through combustion tube 15.

By operation of the drive cylinder 22, the crucible 21 and its supporting structure may be lowered from the interior of combustion tube 15 into the position illustrated in phantom line in FIG. 2 so that the composition to be analyzed can be inserted, removed or replaced and then driven upward into the position for combustion shown in full line in FIG. 2.

Upper cover member 17 is provided with the exhaust pipe or passage 24 for directing the combusted gas into combusted gas feed tube 9. Cover member 15 is also provided with a central vertical opening for vertically slidably receiving combustion gas feed pipes 5 therethrough. The feed pipes 5 have differing internal diameters (calibers). A conventional change-over mechanism 25 is provided for connecting any one of the feed pipes 5 to combustion gas branch 7. The linear speed of the combustion gas through the selected feed pipe 5 through which combustion gas is provided under pressure, will vary according to the diameter of the selected pipe 5. Therefore, by connecting the proper feed pipe 5 to the combustion gas branch 7, the linear speed at which the oxygen gas is directed to the composition in crucible 21 can be changed as desired.

The feed pipes 5 are enclosed within a larger diameter pipe 26 which extends through the upper cover member 17 from below change-over mechanism 25. A drive cylinder 29 is provided above change-over mechanism 25 for controlling the vertical height of pipe 26 and the feed pipes 5 therein. In this way, the outlets a of the feed pipes 5 may be freely moved to a desired distance from the composition to be analyzed which is within crucible 21. The distance which the combustion gas (oxygen) from the feed pipe 5 connected to the combustion gas branch 7 must flow within combustion tube 15 before impinging upon or combusting with the composition being analyzed can thereby be easily controlled. Thus, by controlling change-over mechanism 25 and drive cylinder 29, the amount and speed of the oxygen directed to the composition in crucible 21 from combustion gas branch 7 can be controlled.

Flow control valves 27 and 28 are respectively provided in gas passage branches 7 and 8. By controlling the gas flow through one or both of these valves, the relative flow, or stated another way, the ratio of the gas flow, in branches 7 and 8 can be controlled. A controlling mechanism 30, the details of which would be obvious to one of ordinary skill in the art are not provided herein for the sake of brevity, is provided for controlling the operation of flow control valves 27 and 28, change-over mechanism 25 and drive cylinder 29 so that the ratio of oxygen gas flowing through branches 7 and 8 and the speed and quantity of oxygen provided to the composition to be analyzed can be controlled according to the particular composition to be analyzed and according to the stage of combustion of the composition, to provide the most desirable conditions for combustion and performance of the analysis.

In some instances, only one of the means for controlling the oxygen to the composition may be utilized. In other instances, depending on the type and quantity of the composition in the crucible 21, another or a combination of these means may be utilized for controlling the speed and quantity of oxygen provided to the composition.

For example, in one mode of operation, the desired conditions of combustion are provided as follows:

(1) At first, the quantity of oxygen gas fed from the supply source 2 to branches 7 and 8 is set depending on the kind of composition to be analyzed by adjustment of flow controller 12.

(2) Then in the initial period of combustion, the quantity of oxygen gas serving as the carrier which flows through branch 8 is reduced by means of flow controller 28, whereby the relative quantity of oxygen gas used for combustion fed through branch 7 is increased to promote the start of combustion.

(3) Subsequently, the quantity of oxygen gas serving as the carrier flowing in branch 8 is increased, whereby the relative quantity of oxygen gas provided through branch 7 for combustion is decreased in order to prevent the generation of dust at the composition and to prevent the composition in liquid form from splashing out of the crucible.

(4) Finally, in the final stages of combustion, the quantity of oxygen gas serving as the carrier passing through branch 8 is again decreased to a level substantially the same as at the start of combustion in order to increase the amount of oxygen serving as combustion gas, in order to complete the combustion process.

Alternatively, the ratio of the quantity of oxygen gas flowing through branch 7 and used for combustion to that oxygen gas serving as the carrier fed through branch 8 can also be changed by changing the caliber of the feed pipe 5 connected to branch 7 by means of change-over mechanism 25 and/or moving the feed pipes 5 toward or away from crucible 21 by means of driving device 29. For example, the state of combustion can be slowed or promoted and the amount of carrier gas correspondingly increased or decreased by appropriate selection of the calibre of the feed pipe 5 with change-over mechanism 25. Additionally, the amount of oxygen provided to the composition for combustion can be increased or decreased by moving the feed pipes 5 respectively toward or away from the composition by means of drive cylinder 29.

Also, as indicated above, the speed at which the oxygen is provided to the composition for combustion can be increased or decreased by respectively decreasing or increasing the caliber of the feed pipe 5 connected to branch 7.

Thus, by appropriate control of valves 27 and 28, change-over mechanism 25 and drive cylinder 29 by controlling mechanism 30, the following preferable combustion conditions can be attained:

(1) At the start of combustion, the quantity of the gas used for combustion as well as the linear speed of the gas used for combustion, provided through branch 7, are increased in order to improve the initiation of combustion.

(2) Once combustion has been fully and stably established, the speed of the combustion gas provided through branch 7 is markedly reduced and the quantity of gas for combustion provided through branch 7 is slightly reduced, so as to prevent the generation of dust and the splashing of liquid from the crucible.

(3) In the final stages of combustion, the linear speed of combustion gas provided from branch 7 is further reduced to prevent the generation of dust and the splashing of liquid from the crucible while the quantity or rate at which combustion gas is provided from branch 7 is increased in order to promote the completion of the combustion process.

The extent of the increases and decreases in combustion gas amounts and linear speed should properly vary according to the kind and size of the composition being analyzed in addition to the stage of the combustion process at a particular point in time.

Although only one preferred embodiment of the present invention has been described in detail herein, it will be appreciated by those skilled in the art that many modifications and variations of this embodiment may be made fully within the scope of the invention, which is limited only by the appended claims. For example, for purposes of controlling the relative amount of flow of oxygen through branches 7 and 8, either one of the flow controllers 27 and 28 can be omitted.

What is claimed is:

1. An apparatus for analyzing constituent elements in a metal composition, comprising:
    a combustion furnace having means for holding therein in a composition position a quantity of a metal composition to be analyzed containing one or both of carbon and sulfur and means for combusting the sulfur and carbon in the metal composition held in said furnace;
    means for feeding a flow of oxygen gas to said furnace at a constant rate; said feeding means including portion directing means for directing a portion of the flow of oxygen gas into said furnace toward said composition position into reactive contact with the quantity of metal composition held in said furnace so as to promote oxidation of the carbon and sulfur in the quantity of metal composition held in said furnace so as to produce carbon dioxide and sulfur dioxide gas, and remainder directing means for directing the remainder of the constant flow of oxygen gas not included in the portion thereof directed into said furnace by said portion directing means, separately from said portion directing means into said furnace symultaneously with the direction of the portion of the oxygen gas into said furnace by said portion directing means;
    a gas analyzer, including means for analyzing sulfur dioxide gas and carbon dioxide gas;
    means, including an outlet conduit extending between said furnace and said gas analyzer, for directing the sulfur dioxide and carbon dioxide gas produced in said furnace into said gas analyzer, said remainder directing means including means for directing the remainder of the constant flow of oxygen gas into said furnace so as to carry the carbon dioxide and sulfur dioxide gas produced in said furnace therewith into said outlet conduit so as to carry the carbon dioxide and sulfur dioxide gas produced in said furnace in said outlet conduit from said furnace into said gas analyzer to be analyzed by said analyzing means; and
    means for changing the ratio of oxygen gas flow in the portion to the oxygen gas flow in the remainder, said ratio changing means comprising means for changing each of the amount of the oxygen gas flow in the portion and the amount of the oxygen gas flow in the remainder flowing symultaneously.

2. An apparatus as in claim 1, wherein said portion directing means includes a plurality of feed pipes of different calibers opening into said furnace toward said composition position, and said ratio changing means includes means, including means for selectively, changably directing the portion of the flow of oxygen gas into said furnace toward said composition position into reactive contact with the quantity of metal composition held in said furnace, through any of said plurality of feed pipes.

3. An apparatus as in claim 1, wherein said portion directing means includes at least one feed pipe opening into said furnace for directing the portion of the flow of oxygen gas to said composition position, said ratio changing means including drive means for alternatively moving said at least one feed pipe toward or away from said composition position so as to change the portion of the flow of oxygen gas directed to the quantity of metal composition held in said furnace.

4. An apparatus as in claim 2, wherein said ratio changing means further comprises drive means for alternatively moving said plurality of feed pipes toward or away from said composition position.

5. An apparatus as in claim 1, wherein said feeding means comprises an oxygen supply conduit having a first end for connection to a source of oxygen gas and a second end branched into a first branch, forming said portion directing means, for directing the portion of the flow of oxygen gas toward said composition position into reactive contact with the quantity of metal composition held in said furnace, and a second branch, forming said remainder directing means, for directing the remainder of the flow of oxygen gas into said furnace so as to carry the carbon dioxide and sulfur dioxide gas produced in said furnace therewith into said outlet conduit, said ratio changing means including means for controlling the ratio of oxygen gas flow in said first branch to oxygen gas flow in said second branch.

6. An apparatus as in claim 5, wherein said ratio controlling means comprises a first adjustable valve in said first branch and a second adjustable valve in said second branch.

7. An apparatus as in claim 6 wherein said feeding means further comprises a flow controller in said outlet conduit for controlling the rate of flow of oxygen gas between said first and second ends of said oxygen supply conduit.

8. An apparatus as in claim 5, wherein said ratio changing means comprises:
    a plurality of feed pipes of different calibers located at the end of said first branch, opening into said furnace toward said composition position;
    means for selectively changably directing the oxygen gas in said first branch into said furnace through any one of said plurality of feed pipes;
    drive means for alternatively moving said plurality of feed pipes toward or away from the quantity of the metal composition held in said furnace; and
    first and second controllers respectively disposed in said first and second branches for controlling the respective rates of flow of oxygen gas therethrough;
    said ratio controlling means including a controlling mechanism coupled to said means for selectively changeably directing, said drive means and said first and second flow controllers, for automatically controlling the ratio of oxygen gas flow in said first branch to oxygen gas flow in said second branch, the rate at which oxygen gas is directed to the quantity of metal composition held in said furnace through one of said plurality of pipes and the speed of oxygen flow from said first branch at the quantity of metal composition after passing through said one of said plurality of feed pipes.

* * * * *